(12) United States Patent
Hawkins

(10) Patent No.: US 9,254,264 B2
(45) Date of Patent: Feb. 9, 2016

(54) COMPOSITIONS AND USES THEREOF

(75) Inventor: John Hawkins, Sough Staffordshire (GB)

(73) Assignee: BIOSUSPENSIONS LIMITED, Shepshed, Leicestershire (GB)

( * ) Notice: Subject to any disclaimer, the term of this patent is extended or adjusted under 35 U.S.C. 154(b) by 77 days.

(21) Appl. No.: 12/865,922

(22) PCT Filed: Feb. 6, 2009

(86) PCT No.: PCT/GB2009/000332
§ 371 (c)(1),
(2), (4) Date: Jan. 17, 2011

(87) PCT Pub. No.: WO2009/098469
PCT Pub. Date: Aug. 13, 2009

(65) Prior Publication Data
US 2011/0117019 A1    May 19, 2011

(30) Foreign Application Priority Data

Feb. 6, 2008  (GB) .................................. 0802148.7
Feb. 6, 2008  (GB) .................................. 0802149.5
Feb. 6, 2008  (GB) .................................. 0802150.3

(51) Int. Cl.
| | |
|---|---|
| A61K 9/10 | (2006.01) |
| A23L 1/035 | (2006.01) |
| A23L 1/30 | (2006.01) |
| A61K 31/167 | (2006.01) |
| A61K 47/12 | (2006.01) |
| A61K 47/24 | (2006.01) |
| A61K 47/26 | (2006.01) |

(52) U.S. Cl.
CPC . *A61K 9/10* (2013.01); *A23L 1/035* (2013.01); *A23L 1/30* (2013.01); *A61K 31/167* (2013.01); *A61K 47/12* (2013.01); *A61K 47/24* (2013.01); *A61K 47/26* (2013.01)

(58) Field of Classification Search
CPC combination set(s) only.
See application file for complete search history.

(56) References Cited

U.S. PATENT DOCUMENTS

| | | | |
|---|---|---|---|
| 5,597,562 A | 1/1997 | Nomura et al. | |
| 2002/0106368 A1 | 8/2002 | Bot et al. | |
| 2007/0087104 A1 * | 4/2007 | Chanamai | A23D 7/003 426/602 |

FOREIGN PATENT DOCUMENTS

| | | |
|---|---|---|
| EP | 0659347 A1 | 6/1995 |
| FR | 2754193 A1 | 4/1998 |
| WO | WO 0050007 A1 * | 8/2000 |
| WO | 01/32036 | 5/2001 |
| WO | 2005/007133 | 1/2005 |
| WO | 2007026271 A1 | 3/2007 |
| WO | 2008/002121 | 1/2008 |

OTHER PUBLICATIONS

Yamanka et al., J. Agric. Food Chem. 2008, 56, 11432-11440.*

* cited by examiner

*Primary Examiner* — Michael G Hartley
*Assistant Examiner* — Robert Cabral
(74) *Attorney, Agent, or Firm* — Robert C. Netter, Jr.; Dann, Dorfman, Herrell & Skillman

(57) ABSTRACT

The present invention provides structured surfactant systems comprising water and from 0 to saturation of sugar, together with sufficient surfactant to form a structure capable of suspending solids, wherein the surfactant comprises a mixture of: (i) a major portion of at least one sugar ester and/or a triterpenoid glycoside (saponin) having an HLB greater than 10; and (ii) a minor portion of at least one fatty acid and/or lecithin. The invention further provides pharmaceutical compositions comprising a structured surfactant system of the invention and a pharmaceutical or veterinary active ingredient.

21 Claims, No Drawings

COMPOSITIONS AND USES THEREOF

The present application is §371 application of PCT/GB2009/000332, filed Feb. 6, 2009, which claims priority to GB Application No. 0802148.7, filed Feb. 6, 2008; GB Application No. 0802149.5, filed Feb. 6, 2008; and GB Application No. 0802150.3, filed Feb. 6, 2008. The entire disclosure of each of the foregoing applications is incorporated by reference herein.

FIELD OF INVENTION

The present invention relates to structured suspending systems, which are particularly suitable for pharmaceutical, veterinary and analytical use.

The invention is especially relevant to aqueous structured surfactant systems capable of suspending pharmaceutical and veterinary active materials for internal use. It is suitable for preparations intended for oral, parenteral or pulmonary administration and also for food and beverages which comprise a liquid phase containing suspended solids.

The invention is also relevant generally to the suspension of solids or water-immiscible liquids in aqueous, structured surfactants, for example in household or industrial cleaning preparations, personal care formulations, and also for agricultural or horticultural applications, especially where strongly ionised surfactants are undesirable.

BACKGROUND

Oral medicaments are usually in the form of tablets, pills or capsules, despite the fact that many people, especially children, the elderly and certain dysphagics, have difficulty swallowing them. It is probable that most people would prefer to take medicines in the form of a pleasant tasting liquid, if they were available in such a form. Parenteral medicaments, including intravenous, intramuscular and intraperitoneal preparations must normally be administered in liquid form, which causes serious problems, restricting the use of many products. A variety of inhaled preparations are also administered in liquid form, using a range of nebulisers and pressurised devices.

The main reason why more medicines are not available in liquid form is that the majority are insoluble, or only sparingly soluble, in water or any other acceptable solvent. To be administered as liquids they would have to be suspended. However medicinal suspensions undergo sedimentation on standing, leading to a risk of under or overdosing, if instructions to shake the bottle thoroughly are not fully complied with.

A further problem is that only relatively low concentrations of solids can be suspended, without the product becoming unacceptably viscous. For these reasons the use of oral suspensions has largely been confined to paediatric medicine, where only a fraction of the adult dose may be required. Thus for example suspensions of paracetamol are widely used for treating infants, but no adult equivalent is available. Also, for similar reasons, many parenteral preparations have to be administered in larger than desired volumes over longer than desirable time frames, to achieve the necessary therapeutic dosing range of the drug.

Attempts to solve the problem of dispersing pharmaceuticals in water have hitherto usually involved the use of thickeners (e.g. gums or polymers) to raise the viscosity of the liquid medium. Thickeners only retard sedimentation. They do not provide stable suspensions. Thus, for example, paediatric suspensions of paracetamol, although very viscous, are not stable.

The only alternative to the use of viscosifiers for suspending pharmaceuticals has been to make colloidal dispersions. The latter contain particles of about 1 micron or smaller, which are prevented from sedimenting by Brownian motion. Such systems are incapable of dispersing relatively coarse particles. Since colloidal particles tend to increase in size with time by Ostwald ripening and/or agglomeration, colloidal suspensions are liable to undergo sedimentation.

In contrast to the foregoing, structured suspending systems depend on the rheological properties of the suspending medium to immobilise the particles, irrespective of size. This requires the suspending medium to exhibit a yield point, which is higher than the sedimenting or creaming force exerted by the suspended particles, but low enough to enable the medium to flow under externally imposed stresses, such as pouring and stirring, like a normal liquid. The structure reforms sufficiently rapidly to prevent sedimentation, once the agitation caused by the external stress has ceased. The only structured systems, sufficiently effective to have found widespread application, have been based on aqueous surfactant mesophases.

The terms "structured system", "structured surfactant system", "structured suspending system" as used interchangeably herein mean a composition comprising water, surfactant and any structurants required to impart suspending properties to the surfactant. These components together form a mesophase, or a dispersion of a mesophase in a continuous aqueous medium, which has the ability to suspend non-colloidal, water-insoluble particles, while the system is at rest, without sedimentation.

Structured surfactants generally comprise an $L_\alpha$-phase, in which bilayers of surfactant are disposed with the hydrophobic "tail groups" of the surfactant on the inside and the hydrophilic "head groups" on the outside of the bilayer. The bilayers lie in a parallel or concentric arrangement, usually alternating with layers of an aqueous medium.

$L_\alpha$-phases are sometimes referred to in the art as G-phases. They are commonly characterised by the textures observed under the polarising microscope and/or by small angle X-ray diffraction, which usually shows peaks indicative of lamellar symmetry, e.g. first, second and sometimes higher order peaks with a d-spacing in a simple integral ratio 1:2:3. The d-spacing is given by the formula $2\pi/Q$, where Q is the momentum transfer vector.

Structured suspending systems typically comprise dispersed lamellar, spherulitic and/or expanded lamellar phases. Dispersed lamellar phases are two phase systems, in which domains of a lamellar phase are dispersed in, or interspersed with, an aqueous phase to form a gel. They are described in EP 0 086 614.

Spherulitic phases comprise spheroidal bodies, usually referred to in the art as spherulites, with an onion-like structure comprising concentric shells of surfactant. The spherulites usually have a diameter in the range 0.1 to 15 microns and are dispersed in an aqueous phase in the manner of a classical emulsion, but interacting to form a structured system. Spherulitic systems are described in more detail in EP 0 151 884.

The third type of structured system is the expanded $L_\alpha$-phase, which is a single phase having a wider d-spacing than conventional $L_\alpha$-phase. Conventional $L_\alpha$-phases, contain 60 to 75% by weight surfactant and have a d-spacing of 4 to 7 nanometers. Attempts to suspend solids in such phases result in stiff pastes which are either non-pourable, unstable or both.

Expanded $L_\alpha$-phases have a d-spacing greater than 8, e.g. 10 to 100 nanometers. They may be prepared by adding electrolyte to aqueous surfactants at concentrations below those required to form a normal $L_\alpha$-phase. Expanded $L_\alpha$-phases are described in more detail in EP 0 530 708.

Most structured surfactants require the presence of a structurant, as well as surfactant and water in order to form systems capable of suspending solids. The term "structurant" is used herein to describe any non-surfactant capable, when dissolved in water, of interacting with surfactant to form or enhance (e.g. increase the yield point of) a structured system. It is typically a surfactant-desolubiliser, e.g. an electrolyte. However, certain relatively hydrophobic surfactants such as isopropylamine alkyl benzene sulphonate are self-structuring, and can suspend solids in the absence of any structurant. Self structuring systems are described in EP 0 414 549.

WO 01/00788 describes the use of carbohydrates such as sugars and alginates as deflocculants in structured surfactant compositions. The latter comprise surfactant, water and electrolyte in proportions adapted to form flocculated two-phase structured surfactant systems in the absence of the carbohydrate.

The use of deflocculant polymers to prepare clear spherulitic or other dispersed $L_\alpha$ structured systems, by shrinking the spherulites or other $L_\alpha$ domains to a size below the wave length of visible light, has been described in WO 00/63079. The latter also describes the use of sugar to modify the refractive index of the aqueous phase as an alternative means of obtaining clear liquids.

It is known from WO 01/05932 that carbohydrates can interact with surfactants to form suspending structures. Such systems generally exhibit even greater d-spacings than the electrolyte-structured expanded $L_\alpha$-phases, described in EP 0 530 708. The d-spacings of the sugar-structured systems, described in WO 01/05932, are typically greater than 15 nm, and may, for example, be as high as 50 nm. Such systems are generally clear or translucent.

In addition to their use to suspend dispersed particles, structured systems may be used in solid-free liquid formulations, as taught in U.S. Pat. No. 4,244,840, e.g. to modify the rheology and/or appearance of the composition.

Several of the above publications have suggested the use of structured surfactants to suspend pharmaceutical ingredients for topical application. However none of the structured systems described hitherto has proved acceptable to the pharmaceutical industry for medicines for internal use.

The only structured systems to have found practical application have been in laundry detergents, hard surface cleaners and personal care formulations such as shampoos. These rely to a substantial extent on anionic surfactants, and especially sulphonates and sulphates, which readily form suspending structures, but which are not acceptable for oral administration.

The surfactants approved for pharmaceutical and food use are almost exclusively non-ionic and do not readily form structured systems. One problem with non-ionic surfactants is high temperature instability of the lamellar mesophases.

WO2005007133 referred to the use of non-ionic structured systems to suspend various active ingredients, including pharmaceuticals and described a paracetamol suspension, which could contain up to 20% paracetamol. However the formulation required the presence of 15% by weight of surfactant, which is undesirably high for a product intended for internal use, particularly as the surfactant system contains high levels of ethoxylate. The composition has an unpleasant bitter taste and is somewhat physically aggressive to biological systems. Like most conventional suspensions with high loading of active material, the formulation is too viscous for convenient dispensing.

The specification teaches that at least 30% of bent chain groups are essential for high temperature stability. The only compounds with bent chain groups, as defined in WO2005007133, that are accepted for pharmaceutical use are oleyl compounds, which can give rise to rancid odours and flavours on standing. High levels of oleate in products intended for oral ingestion generally require the inclusion of antioxidants. The definition of "bent chain" excludes polyunsaturated groups, such as linolenyl groups and other omega 3 groups which would be preferable to oleyl.

As a result of these problems, and despite the obvious deficiencies of the existing methods, structured systems have still not found an application in the pharmaceutical industry.

SUMMARY OF INVENTION

The inventors have discovered that a mixture of a sugar ester or triterpenoid glycoside (saponin) having a relatively high HLB (e.g. above 10) with a minor proportion of a fatty acid forms a uniquely robust, low viscosity system with suspending properties at substantially reduced surfactant levels, compared with the prior art. The novel system is tasteless and self-structuring in water, but tolerates the presence of high levels of sugar, if the latter is desired, e.g. to mask any unpleasant taste of the suspended solids, or raise the yield point.

By "HLB" we mean the hydrophilic-lipophilic balance in respect of a surfactant. The HLB may be measured using methods well known in the art, for example see Griffins experimental procedure, Griffins numerical procedure and Greenwalds water number given in: '*Guide To The Surfactants World*', X. Domingo, Ed. Proa., Barcelona, Spain (1995) ISBN 84-8256-096-4, pages 225-233.

The inventors have further discovered that, in the substantial absence of ethoxylated surfactant, it is possible to formulate high temperature stable products capable of forming pourable suspensions of pharmaceutical active ingredients with pharmacologically acceptable surfactants without the use of bent chains, such as oleyl groups, contrary to the teaching of WO2005007133. Such products can be prepared at reduced surfactant levels compared with the prior art and at a lower viscosity. They also have a substantially improved flavour.

In particular, the inventors have discovered that a mixture of a sugar ester or triterpenoid glycoside (saponin) having a relatively high HLB (e.g. above 10) with a minor proportion of a fatty acid forms a uniquely robust, low viscosity system with suspending properties, which is tasteless and self-structuring in water, but which tolerates the presence of high levels of sugar, if the latter is desired, e.g. to mask any unpleasant taste of the suspended solids.

A first aspect of the invention thus provides a structured surfactant system comprising water and from 0 to saturation of sugar, together with sufficient surfactant to form a structure capable of suspending solids, characterised in that the surfactant comprises a mixture of:
  (i) a major portion of at least one sugar ester or triterpenoid glycoside (saponin), having an HLB greater than 10; and
  (ii) a minor portion of at least one fatty acid and/or lecithin.

The invention further provides an aqueous, non-ionic, structured surfactant system, which is substantially free from alkoxylated surfactant and wherein at least 75% by weight of the hydrophobic groups are saturated and/or polyunsaturated fatty alkyl or alkenyl groups. Thus, in a preferred embodiment the invention provides an aqueous, non-ionic structured surfactant system as aforesaid, comprising water and from 0 to saturation of sugar, together with sufficient surfactant to form a structure capable of suspending solids, characterised in that the surfactant comprises a mixture of a major portion of at least one sugar ester or saponin having an HLB greater than 10 and a minor portion of at least one fatty acid.

As indicated above, by the term "structured surfactant system" we include compositions comprising water, surfactant and any structurants required to impart suspending properties to the surfactant. These components together form a mesophase, or a dispersion of a mesophase in a continuous aqueous medium, which has the ability to suspend non-colloidal, water-insoluble particles, while the system is at rest, without sedimentation. By "without sedimentation" we mean that less than 1% by weight of the suspended particles sediment out when the composition is stored at room temperature for two months, preferably less than 0.5% or 0.1%, and most preferably no sedimentation at all (i.e. 0%). Advantageously, such sedimentation levels are achieved over a period longer than two months, for example, at least three months, four months, five months, six months or more. Where some degree of sedimentation has occurred, the composition may be agitated (e.g. shaken) to place the sedimented material back into suspension.

Thus, the invention provides aqueous surfactant compositions suitable for pharmaceutical and/or veterinary use, which are capable of holding water-insoluble particles in suspension for prolonged periods.

In one embodiment, the structured surfactant system is non-ionic, i.e. the surfactant components of the system are non-ionic.

In the following discussion of the invention, unless stated to the contrary, the disclosure of alternative values for the upper or lower limit of the permitted range of a parameter, coupled with an indication that one of said values is more highly preferred than the other, is to be construed as an implied statement that each intermediate value of said parameter, lying between the more preferred and the less preferred of said alternatives, is itself preferred to said less preferred value and also to each value lying between said less preferred value and said intermediate value.

Compositions (i.e. structured surfactant systems) of the invention comprise sufficient total surfactant to form a stable structured surfactant system with any structurant present. This normally requires more than 1% (e.g. more than 1.5%), preferably more than 5%, more preferably more than 7%, most preferably more than 8% by weight of total surfactant based on the total weight of the structured surfactant system. Mixtures of sugar ester with fatty acid, in the absence of structurant, generally form structures at higher concentrations, e.g. greater than 8.5%, more preferably greater than 9%, most preferably greater than 10%, based on the mixture of surfactant and water. Even at these higher levels our preferred mixtures give highly mobile suspensions. In the presence of sugar structurant, structuring of the sugar ester fatty acid mixture is observed at lower concentrations, minimum surfactant concentrations being lower the higher the sugar levels.

The minimum surfactant level for any given system may generally be determined by measuring the viscosity of the system while progressively increasing the surfactant concentration. The viscosity shows a shallow linear increase until a point of inflection is observed, after which it rises more sharply. Suspending systems are obtained at concentrations, as percent by weight total surfactant based on the weight of surfactant, water and structurant, which are above that corresponding to the point of inflection, hereinafter referred to as "$c_i$". Surfactant concentrations are preferably the minimum that will provide an adequate yield point. Higher levels of surfactant are generally undesirable clinically and tend to give higher viscosities. Concentrations of surfactant up to ($c_i$ +5) % are preferred, more preferably up to ($c_i$ +4) %, most preferably up to ($c_i$ +3) %. To ensure adequate yield point, the concentration is preferably more than ($c_i$ +0.1) %. Advantageously, the concentration is between ($c_i$ +0.25) % and ($c_i$ +0.75) %, more preferably between ($c_i$ +0.4) % and ($c_i$ +0.6) %, and most preferably about ($c_i$ +0.5) %.

The concentration of surfactant corresponding to the point of inflection may be determined by methods well known in the art. Thus, the determination of a point of inflection entails progressively increasing the selected independent variable while measuring and plotting the dependent parameter.

For mixtures of a sugar ester with a sorbitan ester, the total surfactant may be less than 5%, still more preferably less than 4%, most preferably less than 3% by weight of the composition.

The preferred mixtures of sugar ester with fatty acid, in the absence of structurant, generally form structures at higher concentrations, e.g. greater than 6%, more preferably greater than 8% most preferably greater than 10%, based on the mixture of surfactant and water. Even at these higher levels our preferred mixtures give highly mobile suspensions.

In the presence of sugar structurant, structuring of the sugar ester fatty acid mixture may be observed at lower concentrations, e.g. down to 3% by weight of the mixture of surfactant and water, minimum surfactant concentrations being lower, the higher the sugar levels. At concentrations of sugar at or near saturation, it is preferred that the minimum surfactant concentration should be at least 3%, preferably at least 5%, more preferably at least 7%, most preferably at least 9% based on the total weight of surfactant and water.

The surfactant component of the compositions of the invention comprises a major portion of at least one sugar ester or triterpenoid glycoside, having an HLB greater than 10, and a minor portion of at least one fatty acid.

By "major portion" and "minor portion" we mean that the surfactant component comprises more of the sugar ester(s) or triterpenoid glycoside than of the fatty acid(s) (measured as a % by weight).

The major portion has an HLB greater than 10, preferably greater than 12, most preferably greater than 14, but preferably less than 30, more preferably less than 20, most preferably less than 17. The high HLB major portion preferably constitutes at least 10%, more preferably at least 30%, still more preferably at least 50%, most preferably at least 60% by weight of the total surfactant.

In one embodiment, the major portion having an HLB greater than 10 is a sugar ester.

The term sugar ester includes saturated and unsaturated fatty esters of sucrose. Suitable esters include octanoates, decanoates, laurates, myristates, palmitates, stearates, behenates, oleates, linoleates, linolenates, erucates and mixtures thereof. Lower molecular weight alkyl esters, such as sucrose laurate, have a slightly soapy taste, but higher mole weight esters, such as stearate and oleate are essentially tasteless. Mixtures comprising the higher homologues with a minor amount of the lower homologues are often preferred for better solubility combined with negligible adverse taste The sugar is preferably a mono or, more preferably, disaccharide sugar, most preferably sucrose, but could for example be fructose, maltose, glucose or invert sugar. Other sugars, which could be used, but are unlikely to be commercially attractive, include, for example, mannose, ribose, galactose, lactose, allose, altrose, talose, gulose, idose, arabinose, xylose, lyxose, erythrose, threose, acrose, rhamnose, fucose, glyceraldehyde, stachyose, agavose and cellobiose or a tri- or tetra-saccharide.

Preferred surfactants may comprise sucrose oleate, but preferably comprise a sucrose ester of a saturated or polyunsaturated fatty acid having at least 8 carbon atoms, preferably more than 10 carbon atoms, but less than 33, preferably less than 20, more preferably less than 18 carbon atoms, such as sucrose laurate, sucrose stearate and/or sucrose linolenate.

The sugar (e.g. sucrose) ester preferably constitutes at least 10%, more preferably at least 30%, still more preferably at least 50%, most preferably at least 60% by weight of the total surfactant.

Sucrose esters consisting substantially of monoester are particularly preferred.

In an alternative preferred embodiment, the high HLB (i.e. >10) surfactant portion is a triterpenoid glycoside (saponin), such as quillaja bark extract. Suitable saponins are commercially available from: Guinness Chemical Products Ltd, London, UK.

The surfactant component of the structured surfactant systems of the invention further comprises a fatty acid or lecithin as a minor portion.

This minor portion is preferably a low HLB non-ionic surfactant. By "low HLB" we mean the minor portion has an HLB less than 10, preferably less than 8, more preferably less than 7, most preferably less than 5. The low HLB surfactant usually has an HLB greater than 1, preferably greater than 2, most preferably greater than 3. The low HLB surfactant may comprise a low HLB sugar ester. However surfactant mixtures consisting entirely of sugar esters tend to be unacceptably viscous. To avoid this it is preferred to use high HLB sugar esters in conjunction with low HLB surfactants with less bulky hydrophilic groups.

In one embodiment, the minor portion comprises or consists of a fatty acid.

The fatty acid may be monounsaturated, saturated or polyunsaturated, having at least 8, preferably at least 10, more preferably at least 12 carbon atoms, but less than 25, more preferably less than 20, most preferably less than 18 carbon atoms, such as decanoic, lauric, myristic, palmitic, stearic, arachidonic, behenic, oleic, palmitoleic, linoleic, linolenic, ricinoleic, erucic, eicosapentaenoic, docosahexaenoic or mixtures thereof, such as the mixtures obtained by the saponification of coconut oil, palm oil, and/or other vegetable oils, fish oils, whale blubber or animal fats. Omega 3 polyunsaturated acids are particularly preferred.

Optionally the surfactant may additionally comprise minor proportions, relative to the fatty acid, of non-alkoxylated glyceryl or sorbitan mono esters of the aforesaid fatty acids, and/or a fatty alcohol.

The fatty acid, optionally together with any other low HLB surfactant, preferably constitutes at least 5%, more preferably at least 10%, still more preferably at least 20%, most preferably at least 30% by weight of the total surfactant.

In an alternative or additional embodiment, the minor portion comprises or consists of lecithin. For example, the lecithin may be present at between 0.1% and 1% by weight of the total surfactant, preferably between 0.1% and 0.3%. It will be appreciated by skilled persons that the lecithin may serve as a stabiliser.

The surfactants constituting the surfactant component of the structured surfactant system preferably have a mean HLB greater than 7, more preferably greater than 8, still more preferably greater than 9, most preferably greater than 9.5, but less than 13, more preferably less than 12, most preferably less than 11.

The surfactants constituting the surfactant component of the structured surfactant system are preferably substantially free from alkoxy groups. That is to say they contain an average of less than 1 alkoxy group, preferably less than 0.5, more preferably less than 0.1, most preferably less than 0.01 alkoxy groups per molecule of surfactant.

The surfactant preferably comprises less than 30% of monounsaturated alkenyl groups, based on the total number of moles of alkyl and alkenyl groups present, more preferably less than 25%, still more preferably less than 20%, even more preferably less than 10%, most preferably less than 1%.

The preferred surfactant systems of the present invention are self-structuring, however the presence of a structurant may be desirable to increase the yield point, improve the flavour of the composition or permit the use of reduced surfactant levels.

By "structurant" we include any non-surfactant capable, when dissolved in water, of interacting with surfactant to form or enhance (e.g. increase the yield point of) a structured system. Exemplary structurants suitable for use in the structured surfactant systems of the invention include surfactant-desolubilising electrolytes and soluble carbohydrates.

Instability may occur if the total surfactant concentration is too close to the phase boundary, e.g. as indicated by $c_i$. Stability can therefore often be improved by increasing the total surfactant. However, high surfactant levels are often undesirable, either for clinical reasons, or to avoid high viscosities. One effect of structurants is usually to lower $c_i$, enabling stable systems to be obtained with less surfactant The structurant preferably consists of or comprises a water-soluble carbohydrate, especially a sugar. The sugar is preferably a mono or, more preferably, disaccharide sugar, most preferably sucrose, but could for example be fructose, maltose, glucose or invert sugar. Other sugars, which can be used, include, for example, mannose, ribose, galactose, lactose, allose, altrose, talose, gulose, idose, arabinose, xylose, lyxose, erythrose, threose, acrose, rhamnose, fucose, stachyose, agavose and cellobiose or a tri- or tetra-saccharide.

In one embodiment, the total concentration of sugar as a structurant is greater than 10%, preferably greater than 30%, more preferably greater than 40%, by weight based on the total weight of the composition, and up to, but preferably less than, saturation. The saturation point may be determined using methods well known in the art.

However, in an alternative embodiment, the structured surfactant system is free of sugar.

The structured surfactant systems of the invention may further comprise one or more electrolytes, for example to improve stability or, if desired, for clinical reasons. The electrolyte could, for example, be sodium chloride, sodium carbonate, potassium chloride, sodium phosphate, sodium citrate or any other surfactant desolubilising electrolyte. Electrolytes are often desirable in parenteral formulations, but less so in oral preparations, on account of taste. The amount of electrolyte is preferably less than 10%, w/w, more preferably less than 5%, even more preferably less than 2%, most preferably less than 1%. For parenteral formulations, levels of electrolyte above 0.3, more preferably above 0.5, most preferably above 0.8% are often desired, especially around that referred to clinically as "isotonic". On flavour grounds it is preferred that the oral compositions are substantially free from electrolyte.

Instead of, or in addition to, using electrolyte to improve stability, it may be preferred to increase the mean HLB of the surfactant, for instance by raising the proportion of the fatty acid or other low HLB surfactant until a stable formulation is obtained. The optimum amount of electrolyte and/or low HLB surfactant can be determined by making incremental additions and measuring the yield point, to determine where the maximum yield point is obtained. Another way of improving stability is to add a small proportion of a more polar surfactant, such as lecithin.

Instability may also occur if the concentration of surfactant and or electrolyte is too high, i.e. too close to the upper phase boundary. This usually manifests itself as flocculation. Relatively small amounts of a carbohydrate such as alginate or sugar, as taught in WO 01/00788, may be added to act as a deflocculant.

Instead of measuring the yield point, or the viscosity, a quick indication of the optimum amount of structurant, or surfactant, is obtained by measuring conductivity. This usually falls with the progressive addition of electrolyte or low HLB non-ionic surfactant, to a first minimum, located within a shallow trough, and then rises to a peak. Occasionally an initial rise in conductivity is observed before the fall to the first minimum. In either event the preferred range is usually within +/−2%, preferably +/−1%, of the first such minimum. Another quick indication of the formation of a structured system is to shake air into the composition and observe the bubbles, which show no tendency to rise in a structured system. For the purpose of this specification "stable" indicates that the suspended solid does not sediment after at least two months storage at room temperature (and preferably after six months storage at room temperature).

Preferred compositions according to the invention are spherulitic. A feature of the preferred self-structuring mixtures of fatty acid and sugar ester in water, in the absence of sugar is the presence of numerous small spherulites, having a diameter at or near the resolving power of the optical microscope. The systems typically give two, apparently independent peaks when examined by small angle X-ray diffraction, one corresponding to a normal spherulitic d-spacing of 7 to 9 nm and one at a much larger d-spacing of 20 to 30 nm. It is believed that the latter may represent the spacing between spherulites, indicating a high degree of uniformity in the size and distribution of the latter.

A feature of the compositions containing high sugar levels is their unusually large repeat spacing, which is greater than 8 nm, preferably greater than 20 nm, more preferably greater than 60 nm, still more preferably greater than 90 nm, most preferably greater than 100 nm, but usually less than 500 nm, preferably less than 400 nm, most preferably less than 200 nm. The repeat spacing may be too high to resolve using small angle X-ray diffraction, and may in some cases be measurable using light or UV diffraction. However, it is not intended to exclude the possibility that some compositions of the invention may comprise expanded lamellar phase, or non-lamellar features.

The levels of carbohydrate may be sufficiently high to inhibit microbiological growth in the medium and sufficient to act as an effective biodegradable, non-allergenic preservative for the composition.

Solvents, such as ethanol, and hydrotropes are not generally required for stability, but can usually be tolerated, in small amounts, if required for functional reasons. If not so required, it is preferred that they be absent. When present it is preferred that they be present in amounts less than 10% by weight of the formulation, more preferably less than 5%, still more preferably less than 3%, most preferably less than 1%.

Preferred structured surfactant systems of the invention comprise or consist of the following components:
(a) Oleic acid, sucrose stearate and water;
(b) Oleic acid, sucrose stearate, sucrose and water;
(c) Oleic acid, sucrose stearate, water and sodium chloride; and/or
(d) Oleic acid, sucrose stearate, sucrose, water and sodium chloride.

In alternatives to the above preferred embodiments, sucrose oleate or sucrose laurate may by used in place of sucrose stearate and/or lauric acid may be used in place of oleic acid.

Advantageously, the structured surfactant systems comprises oleic acid and sucrose stearate at a weight ratio between 1.5:8.5 and 3.5:6.5, preferably between 1.5:8.5 and 2.5:7.5 and most preferably about 2.8. Where present, the sucrose is preferably at a concentration up to 50% by weight, more preferably from 10% to 40% by weight, for example 20% by weight.

The structured surfactant systems of the invention can be used to suspend a wide variety of water-insoluble or sparingly water-soluble medicaments, which are, or can be rendered, sufficiently stable chemically in the presence of the aqueous suspending medium. Any desired particle size may be suspended, although very dense materials may require the selection of a suspending system with a high yield point. Typically particle sizes may be greater than 1 micron, preferably greater than 20 microns, most preferably greater than 100 microns, but usually less than 5 mm, more preferably less than 1 mm, most preferably less than 0.5 mm. Most particles show a tendency to Ostwald ripening in water. This involves an increase in mean particle size with time. A feature of our suspending systems is that the surfactant tends to inhibit particle growth. Moreover, any particle growth that does occur does not, in general, destabilise the system.

The structured surfactant systems of the invention may be used to suspend various encapsulated, or microencapsulated, materials, or inert particles having an active material adsorbed thereon or absorbed therein. The system may also be used to suspend droplets of oils or to co-suspend oil droplets and solid particles. The oil may contain dissolved medicaments. Structured systems are also useful for modifying the rheological properties of aqueous solutions of active ingredients, in the absence of suspended solids or liquids.

Depending on its intended use, the product may optionally contain other common ingredients appropriate to that use (such as flavourants, colourants, preservatives, etc.).

In addition to their use for suspending pharmaceuticals, the systems of the invention are useful in the food and drink industry, e.g. for suspending pieces of solid meat or vegetable in soups or purees, or for suspending particles of fruit in fruit drinks or yoghurts.

A second aspect of the invention provides the use of a structured surfactant system according to the first aspect of the invention to suspend a pharmaceutical or veterinary active ingredient.

Thus, the invention further provides the use of a structured surfactant system according to the first aspect of the invention to deliver a pharmaceutical or veterinary active ingredient to the human or animal body. A related aspect of the invention provides a method of delivering a pharmaceutical or veterinary active ingredient to the human or animal body comprising suspending the active ingredient in a structured surfactant system according to the first aspect of the invention and then administering the structured surfactant system comprising the active ingredient to the human or animal body.

A third aspect of the invention a pharmaceutical composition comprising or consisting of a structured surfactant system according to the first aspect of the invention and a pharmaceutical or veterinary active ingredient (e.g. a drug approved for medical or veterinary use).

It will be appreciated by persons skilled in the art that the active ingredient may be selected from the group consisting of small chemical compounds (e.g. less than 1000 kDa, for example less than 500 kDa), proteins and polypeptides, DNA, oligonucleotides, vectors, cells, vaccines, nanoparticles and biomarkers.

Advantageously, the structured surfactant systems and compositions of the invention have a viscosity at room temperature (e.g. 25° C.) of less than 11 Pascal seconds, for example less than 10 Pascal seconds, 8 Pascal seconds, 6 Pascal seconds, 4 Pascal seconds or less than 2 Pascal seconds.

Viscosity may be determined using methods well known in the art, for example using a variable stress rheometer at normal temperature (e.g. 25° C.) and at a defined shear (for example, 21 reciprocal seconds). Alternatively, a Brookfield viscometer may be used.

In one embodiment, the composition of the third aspect of the invention is a pourable, non-sedimenting suspension of a pharmaceutical or veterinary active agent in a structured surfactant system according to the first aspect of the invention.

By "pourable" we mean that the composition of the third aspect of the invention has a viscosity less than 5 Pascal seconds at room temperature (e.g. 25° C.), preferably less than 3 Pascal seconds, for example less than 2 Pascal seconds.

The active ingredient is preferably a non-soluble and/or particulate.

By "non-soluble" we mean that the active ingredient is capable of forming a 'dispersed system' (for example, solids give suspensions, liquids give emulsions and gases give foams).

As discussed above, any desired particle size may be suspended, although very dense materials may require the selection of a suspending system with a high yield point. Typically particle sizes may be greater than 1 micron, preferably greater than 20 microns, most preferably greater than 100 microns, but usually less than 5 mm, more preferably less than 1 mm, most preferably less than 0.5 mm.

Examples of active ingredients that may be delivered using the structured surfactant systems and compositions of the invention include, but are not limited to:

Antifungal agents including those suitable for oral administration: eg griseofulvin, Agents for the treatment of orthopaedic conditions including steroidal preparations: eg cortisone Azole antifungals e.g. such as itraconazole and saperconazole Low-solubility drugs such as glycogen phosphorylase inhibitors, 5-lipoxygenase inhibitors, corticotropic releasing hormone inhibitors and antipsychotics.

Antiviral (eg HIV) protease inhibitors: eg Saquinavir

Agents with properties that include but not restricted to anxiolytic, anticonvulsant, hypnotic, sedative, skeletal muscle relaxant and amnestic properties: eg diazepam Immunosuppressives: eg Cyclosporin A (CsA), a poorly water soluble immunosuppressant Sandimmune Neoral® (Cyclosporine A), antiretroviral drugs from the protease inhibitor class: Fortovase® (Saquinavir), Norvir® (Ritonavir), Anti-viral agents and coenzymes Agents used in the treatment of oedema associated with congestive heart failure; eg Frusemide Antibiotics including the cephalosporin antibiotics: eg cefixime Drugs used for the treatment of inflammation and pain caused by rheumatoid arthritis: eg ketoprofen Anti-parasitic drug used against protozoan infections eg tinidazole Drugs shown to have potent analgesic and anti-inflammatory activities: eg paracetamol, aceclofenac and ibuprofen Agents with haematological applications in the control of blood clotting: eg Vitamin K3

Poorly water-soluble anticancer drugs, e.g octaethylporphine (OEP), meso-tetraphenyl porphine (mTPP)

Antileukemic agents: eg 6-mercaptopurine

Agents comprising antibody or antibody containing conjugates: eg Campath

Chemotherapeutics including e.g. Taxol (paclitaxel) and related molecules collectively termed taxoids, taxines or taxanes.

Podophyllotoxins and their derivatives and analogues eg etoposide and teniposide.

Camptothecins, including any derivatives and modifications to the basic structure which retain efficacy and preserve the lipophilic character of the molecule, eg Camptothecin, 9-aminocamptothecin, 9-nitrocamptothecin, camptothecin-11 ("Irinotecan"), Topotecan.

Lipophilic anthracyclines including those derivatives with lipophilic modifications including substitutions at the ring hydroxyl group or sugar amino group, eg doxorubicin ("adriamycin").

Other compounds which are lipophilic or can be made lipophilic by molecular chemosynthetic modifications well known to those skilled in the art, for example by combinatorial chemistry and by molecular modelling, and are drawn from the following list: Taxotere, Amonafide, Illudin S, 6-hydroxymethylacylfulvene Bryostatin 1, 26-succinylbryostatin 1, Palmitoyl Rhizoxin, DUP 941, Mitomycin B, Mitomycin C, Porfiromycin, E09, Penclomedine. Interferon α2b, angiogenesis inhibitor compounds, Cisplatin hydrophobic complexes such as 2-hydrazino-4,5-dihydro-1H-imidazole with platinum chloride and 5-hydrazino-3,4-dihydro-2H-pyrrole with platinum chloride.

Vitamin A, vitamin E and its derivatives, particularly tocopherol succinate.

Other compounds useful in the invention include: 1,3-bis (2-chloroethyl)-1-nitrosurea ("carmustine" or "BCNU"), chlorambucil, melphalan, colchicines, combretastatin, gammapentin, temozolamide, 5-fluorouracil, doxorubicin ("adriamycin"), epirubicin, idarubicin, aclarubicin, Bisantrene (bis(2-imidazolen-2-ylhydrazone)-9,10-anthracenedicarboxaldehyde, mitoxantrone, methotrexate, edatrexate, muramyl tripeptide, muramyl dipeptide, lipopolysaccharides, 9-b-d-arabinofairanosyladenine ("vidarabine") and its 2-fluoro derivative, resveratrol, trans-retinoic acids and retinol, Carotenoids, and tamoxifen.

Other compounds useful in the application of this invention include: Palmitoyl Rhizoxin, DUP 941, Mitomycin 13, Mitomycin C, Penclomedine, Interferon α2b, Decarbazine, Lonidamine, Piroxantrone, Anthrapyrazoles, Bleomycin.

Vinca alkaloids and their analogs [Vincristine, Vinorelbine, Vindesine, Vintripol, Vinxaltine, Ancitabine], 6-aminochrysene, and navelbine.

Other compounds useful in the application of the invention are mimetics of taxol, eleutherobins, sarcodictyins, discodermolides and epothiolones.

Poorly water-soluble drugs such as nifedipine.

Agents used in the treatment of vascular disease or hypertension (high blood pressure) or angina (chest pain): eg Filodepine.

It will be appreciated by persons skilled in the art that the compositions of the third aspect of the invention may be administered by any suitable route, for example oral, inhalation (i.e. pulmonary), parenteral, subcutaneous, intravenous, intramuscular, interperitoneal, rectal, vaginal, bladder, intratumoral, peritumoral, topical, aural and ocular administration For example, the structured surfactant systems and compositions of the invention can be administered orally, buccally or sublingually in the form of capsules, ovules, elixirs, solutions or suspensions, which may contain flavouring or colouring agents, for immediate-, delayed- or controlled-release applications. The compositions of invention may also be administered via intracavernosal injection.

In one embodiment of the third aspect of the invention, the composition is a nutraceutical composition, i.e. the active agent is a food or food supplement that provides nutrition.

Exemplary nutraceutical compositions include but are not limited to:

Lipophilic rather than water soluble vitamins (including baby nutrients)

Colloid based formulations for metals

Phytochemicals or phytonutrients (bioactive molecules derived from plants)

insoluble iron salts such as iron phosphates sterols and/or sterol esters with cholesterol reducing properties In a further embodiment of the third aspect of the invention, the composition is a nutritional support product (e.g. for use by people who have difficulty swallowing, people who have specific dietary requirements and/or people who have supplementary dietary needs).

Thus, nutrient suspensions may be provided, optionally suitable for oral, parenteral or enteral administration.

For example, oral nutrient suspensions may be useful to modify uptake of lipids (for example, see Singh et al., 2008, *Prog Lipid Res*, December 14 [Epublication]).

Parenteral or enteral nutrient suspensions may be useful for general surgical patients who require intravenous nutrition either because their gastrointestinal tract is blocked, too short or inflamed or is unable to tolerate oral delivery of nutrients for other reasons. Such suspensions may also be useful for patients receiving chemotherapy, which can lead to poor appetite, mucositis and gastrointestinal failure.

Exemplary nutritional support compositions include but are not limited to those comprising:

Insoluble salts

Fat soluble vitamins

Insoluble fibre preparations

Intact, polymeric macronutrient preparations

The structured surfactant systems and compositions of the invention can also be administered parenterally, for example, intravenously, intra-articularly, intra-arterially, intraperitoneally, intra-thecally, intraventricularly, intrasternally, intracranially, intramuscularly, intravesicularly or subcutaneously, or they may be administered by infusion techniques. The compositions may be suitably buffered (preferably to a pH of from 3 to 9), if necessary.

Compositions suitable for parenteral administration contain anti-oxidants, buffers, bacteriostats and solutes which render the formulation isotonic with the blood of the intended recipient. The composition may be presented in unit-dose or multi-dose containers, for example sealed ampoules and vials. Extemporaneous injection suspensions may be prepared from sterile powders, granules and tablets.

The structured surfactant systems and compositions of the invention can also be administered intranasally or by inhalation and are conveniently delivered from a pressurised container, pump, spray or nebuliser with the use of a suitable propellant, e.g. dichlorodifluoromethane, trichlorofluoromethane, dichlorotetrafluoro-ethane, a hydrofluoroalkane such as 1,1,1,2-tetrafluoroethane (HFA 134A3 or 1,1,1,2,3,3,3-heptafluoropropane (HFA 227EA3), carbon dioxide or other suitable gas. In the case of a pressurised aerosol, the dosage unit may be determined by providing a valve to deliver a metered amount. The pressurised container, pump, spray or nebuliser may additionally contain a lubricant, e.g. sorbitan trioleate.

Alternatively, the structured surfactant systems and compositions of the invention can be administered in the form of a suppository or pessary, or they may be applied topically in the form of a lotion, cream or ointment. They may also be administered by the ocular route or by installation into the bladder.

In a still further embodiment of the third aspect of the invention, the composition is an animal healthcare preparation.

Such preparations may comprise a drug where for administration by oral, pulmonary, parenteral, subcutaneous, intravenous, intramuscular, interperitoneal, rectal, vaginal, bladder, intratumoral, peritumoral, or topical route.

Alternatively, the preparation may be a nutraceutical composition or nutritional support composition (as described above).

A further aspect of the invention provides an imaging contrast media comprising a structured surfactant system according to the first aspect of the invention. Thus, the invention further provides the use of the structured surfactant systems described herein as imaging contrast media.

Examples of such contrast media include but are not limited to compositions comprising:

Image contrast agents containing metal colloids for imaging

Chemically cross-linking copper, bismuth and borne compounds to immunoglobulins (used to target short lived or stable isotopes of these elements to specific tissue for diagnostic or therapeutic applications)

Positron Emission Tomography radiopharmaceuticals

A still further aspect of the invention provides a structured surfactant system according to the first aspect of the invention for use as a support matrix for the analysis of particles involving light collection, including transmission, phase-contrast, fluorescence, fluorescence-lifetime, bioluminescence, chemo-luminescence, anisotropy, light scattering in which particle detection and analysis is enabled by the passage of the support matrix through single or multiple fluidic channels of sufficient dimensions to maintain structured surfactant properties of the system (including fluidic systems and thin film scanning systems). For example, the composition may serve as a support matrix for the analysis of particles by a modified flow cytometer.

Preferably, the particles are analysed by standard fluorescence microscopy.

More preferably, the particles are analysed by confocal laser scanning microscopy, multi-photon excitation laser scanning microscopy or fluorescence microscopy in which the image data collected are subjected to mathematical processing (including deconvolution) to provide depth-specific information.

Conveniently, the light originates the light originates from a genetically encoded construct in a cell to express a fluorescent molecule such as cells manipulated to express a fluorescent molecule, for example green fluorescent protein and/or spectral variants and/or stability variants thereof.

In a further preferred embodiment, the structured surfactant system serves as a support matrix for the multi-dimensional analysis of particles, for example by 3D (x,y,z) imaging, time (kinetic) analysis and lambda (spectral) analysis.

Alternatively, the structured surfactant system may serve as a support matrix for the kinetic analysis of particles.

In a particularly preferred embodiment of the first aspect of the invention, analysis of the particles is performed by high throughput screening.

In another preferred embodiment, the support matrix is for use in calibration, optical alignment or orientation in methodologies requiring the collection of light. For example, the analysis may be for calibration purposes, point-spread function determination and event orientation within optical slices of two or more dimensions.

In an alternative preferred embodiment, the composition serves as a particle mountant.

A still further aspect of the invention provides a structured surfactant system according to the first aspect of the invention for use as a support matrix for the capture, isolation, detection and/or analysis of radioactive particles such as those generated as part of a manufacturing process or released by accident (eg sub-micro to particles >20 microns in aerodynamic diameter) and, for example, having sufficient activity (>100 kBq) to cause acute health hazards or to have radioactive properties of interest to the method and purpose of manufacture.

The composition may also further comprise one or more of the following additives:
1. a cell-fixing chemical, such as paraformaldehyde (PFA);
2. a chemo-attractant, i.e. a chemical agent, exogenously present, eliciting directional motility in a responsive cell;
3. an excipient for the purpose of cell protection or biological modification (such as a growth factor or signalling molecule);
4. an excipient for the purpose of modifying the photophysical and/or photochemical effects of light illumination on cells or reporter molecules (for example, the excipient may reduce photobleaching of fluorescent reporter molecules or enhance photobleaching of extracellular fluorescent reporter molecules); and/or
5. a scintillation fluid permitting the detection of low-energy beta-emitting nuclides (e.g., 3H, 14C, 35S) through the emission of light.

The invention will be illustrated by the following examples, in which all proportions are % by weight, based on the weight of the composition, unless stated to the contrary. In each case the balance was water.

EXAMPLES

Example I 3.6% oleic acid and 8.4% sucrose stearate were heated with water to 85° C. and vigorously mixed in a high shear mixer until the mixture was tasteless, hazily translucent and able to suspend large air bubbles. Under the polarising microscope a very fine granular texture was observed, indicative of a crowded spherulitic system with spherulites having a diameter of 0.5μ or less. Two SAXS peaks were observed at 7 nm and 37.5 nm.

Example II

10% paracetamol powder was stirred into the composition of Example I. The product was a stable mobile suspension, which showed no sedimentation after six months at 45° C.

Example III

| Oleic acid | 2.55 |
| Sucrose stearate | 5.95 |
| Sucrose | 44.89 |

The above ingredients were mixed with water at 85° C. using a high shear mixer. The product was a stable, homogeneous, structured system which was spherulitic when viewed under the polarising microscope, showing a characteristic texture of packed discs, of 1 to 2μ diameter, each showing clearly defined extinction crosses. The lamellar repeat spacing, as shown by small angle X-ray scattering was very large, being greater than 100 nm. On stirring with 10% paracetamol a stable, mobile, pleasant tasting suspension was formed which has shown no separation after four months.

Example IV

To determine the optimum ratio of fatty acid to sugar ester a series of samples was prepared with various ratios of oleic acid to sucrose stearate, and each was dissolved in water at a total concentration of 12% by weight. Suspending power was checked by shaking, and observing the size of air bubbles, if any, that could be stably suspended. Suspending systems were observed at weight ratios between 1.5:8.5 and 3.5:6.5, with best suspending observed between 1.5:8.5 and 2.5:7.5, especially around 2:8.

Example V

The phase boundary between the $L_1$ (non-suspending micellar) and suspending spherulitic phases was plotted for the system 1:4 w/w oleic acid:sucrose stearate, water, 0 to 50% by weight sucrose. The minimum concentrations of surfactant required to provide a suspending system are shown in the following table.

| % sucrose | % surfactant |
|---|---|
| 0 | 12 |
| 10 | 10.5 |
| 20 | 10 |
| 30 | 9.5 |
| 40 | 9 |
| 50 | 8.5 |

Example VI

The viscosity of compositions comprising water, 20% sucrose, 7 to 11% surfactant (1:4 oleic acid:sucrose stearate), was measured on a Brookfield viscometer at 21 s$^{-1}$ and 20° C. The results are shown in the following table.

| % surfactant | cps |
|---|---|
| 7.0 | 66 |
| 7.5 | 127 |
| 8.0 | 302 |
| 9.0 | 469 |
| 10.0 | 704 |
| 10.5 | 1370 |
| 11 | 2600 |

A clear point of inflection occurs at the phase boundary (10% surfactant, as shown in example V).

Example VII

The 10.5% surfactant system from Example VI was mixed with 10% by weight, based on the total weight of the mixture, of paracetamol. The mixture (9.45% surfactant, 18% sucrose, 10% paracetamol) was non-sedimenting and had Brookfield viscosity of 1560 cps.

Examples VIII to XI

|  | VIII | IX | X | XI |
|---|---|---|---|---|
| Paracetamol | 20.0 | 20.0 | 20.0 | 20.0 |
| Sucrose | 52.0 | 52.0 | 52.0 | 52.0 |
| Sucrose mono stearate | 1.5 | 2.0 | 2.1 | 1.8 |
| Sorbitan mono laurate | 1.5 |  |  | 0.6 |
| Sorbitan mono oleate |  | 1.0 |  | 0.6 |
| Oleic acid |  |  | 0.9 |  |

The above formulations were prepared by adding the ingredients in the order shown, with gentle stirring to avoid air entrainment, starting with 67% w/w aqueous sugar solution.

The products were readily pourable and showed no sign of separation after three months standing at laboratory ambient temperature, 45° C. or 5° C. The suspending system (the composition without the paracetamol) was spherulitic when viewed under a polarising microscope. The repeat spacing by small angle X-ray diffraction was greater than 100 nm.

Examples VIII, XI and XI are included for comparison only; they do not constitute structured surfactant systems of the invention.

Example VIII

The 11% surfactant system from Example VI is mixed with 10% by weight, based on the total weight of the mixture, of kaolin. Kaolin is used as an exemplary non-soluble, particulate material to demonstrate the ability of the structured surfactant system to maintain a suspension.

The mixture is non-sedimenting over three months.

Example IX

Example VIII is repeated using 11.5% by weight total surfactant. The mixture is non-sedimenting after three months.

Examples X-XVII

Four portions of the 10.5% surfactant system and four portions of the 11% surfactant system from Example VI are each mixed with 10% by weight, based on the total weight of the mixture, of kaolin and 0.25%, 0.5%, 0.75% and 1% respectively sodium chloride. The mixtures are non-sedimenting over three months.

Examples XVII-XLI

Examples X-XVII are repeated using surfactants with a ratio of oleic acid:sucrose ester of 2:7, 2:6 and 2:5 respectively. The mixtures are non-sedimenting over three months Examples XLII-LXXVI Examples VII to XLI are repeated using sucrose oleate in place of sucrose stearate. The products are non-sedimenting after three months.

Examples LXXVII-CXI

Examples VII to XLI are repeated using sucrose laurate in place of sucrose stearate. The products are non-sedimenting after three months.

Examples CXII-CCXVII

Examples VII to CXI are repeated using lauric acid in place of oleic acid. The products are non-sedimenting over three months.

Examples CCXVIII-CCXXVII

The following formulations are non-sedimenting over three months.

|  | 218 | 219 | 220 | 221 | 222 | 223 | 224 | 225 | 226 | 227 |
|---|---|---|---|---|---|---|---|---|---|---|
| Sucrose | 0 | 44 | 45 | 0 | 0 | 0 | 0 | 40 | 40 | 0 |
| Sucrose monostearate | 9 | 6.5 | 6 | 0 | 0 | 0 | 5 | 0 | 3 | 9 |
| Sucrose monolaurate | 0 | 0 | 0 | 10 | 10 | 0 | 5 | 3 | 0 | 0 |
| Sucrose monooleate | 0 | 0 | 0 | 0 | 0 | 10 |  | 4 | 4 | 0 |
| Oleic acid | 4 | 3 | 2.6 | 0 | 0 | 3 | 3 | 0 | 2 | 4 |
| Lauric acid | 0 | 0 | 0 | 3 | 3 | 0 |  | 4 | 1 |  |
| Sodium chloride | 0 | 0 | 0.5 | 0 | 0.5 | 0.75 | 0.25 | 0.5 | 0.25 | 1 |

Additional Examples

Examples CCXVIII-CCXXVII are repeated additionally containing lecithin as a 'stabiliser' ('soy lecithin powder'—available from Lucas Meyer Cosmetics France) at a concentration of 0.1, 0.2 and 0.3% by weight, based on the total weight of the mixture.

The invention claimed is:

1. A structured surfactant system comprising water and from 0 to saturation of sugar, together with a sufficient amount of surfactant to form a structure which suspends solids substantially without sedimentation for at least two months at room temperature, wherein the surfactant comprises a mixture of:
   (i) a major portion of at least one sugar ester and/or a triterpenoid glycoside having a hydrophilic-lipophilic balance (HLB) greater than 10; and
   (ii) a minor portion of at least one fatty acid and/or lecithin, wherein said surfactant comprises less than 30% of monounsaturated alkenyl groups based on the total number of moles of alkyl and alkenyl groups present.

2. A structured surfactant system according to claim 1 wherein the surfactant is non-ionic.

3. A structured surfactant system according to claim 1 wherein the total concentration of surfactant is greater than the point of inflection ($c_i$) or between ($c_i$+0.5)% and ($c_i$+10)%.

4. A structured surfactant system according to claim 1 wherein the major portion has an HLB greater than 12 and/or less than 20 or greater than 14 and/or less than 17.

5. A structured surfactant system according to claim 1 comprising a sugar ester or a sugar ester selected from the group consisting of sucrose oleate, sucrose laurate, sucrose stearate and sucrose linolenate.

6. A structured surfactant system according to claim 1 wherein the concentration of sugar ester is greater than 10% or greater than 50% based on the total concentration of surfactant.

7. A structured surfactant system according to claim 1 wherein the minor portion has an HLB less than 8 and/or greater than 2 or less than 5 and/or greater than 3.

8. A structured surfactant system according to claim 1 comprising a fatty acid.

9. A structured surfactant system according to claim 8 wherein the fatty acid constitutes at least 10% or at least 30% by weight of the total surfactant.

10. A structured surfactant system according to claim 1 comprising lecithin.

11. A structured surfactant system according to claim 10 wherein the lecithin constitutes between 0.1% and 1% by weight of the total surfactant.

12. A structured surfactant system according to claim 1 wherein the mean HLB of the surfactants is between 7 and 13 or between 9.5 and 11.

13. A structured surfactant system according to claim 1 comprising a structurant or a sugar.

14. A structured surfactant system according to claim 13 wherein the total concentration of structurant is greater than 10%.

15. A structured surfactant system according to claim 1 wherein the system is spherulitic.

16. A structured surfactant system according to claim 1 comprising or consisting of the following:
   (a) Oleic acid, sucrose stearate and water;
   (b) Oleic acid, sucrose stearate, sucrose and water;
   (c) Oleic acid, sucrose stearate, water and sodium chloride; and/or
   (d) Oleic acid, sucrose stearate, sucrose, water and sodium chloride.

17. A pharmaceutical composition comprising or consisting of a structured surfactant system according to claim 1 and a pharmaceutical or veterinary active ingredient.

18. A composition according to claim 17 wherein the active ingredient is non-soluble and/or particulate.

19. An imaging contrast medium comprising a structured surfactant system according to claim 1.

20. A structured surfactant system comprising water and from 0 to saturation of sugar, together with a sufficient amount of surfactant to form a structure which suspends solids, wherein the surfactant comprises a mixture of:
   (i) a major portion of at least one sugar ester and/or a triterpenoid glycoside having a hydrophilic-lipophilic balance (HLB) greater than 10; and
   (ii) a minor portion of at least one fatty acid and/or lecithin, wherein the structured surfactant system comprises a pharmaceutical or veterinary active ingredient as a suspended solid, and
   wherein said surfactant comprises less than 30% of monounsaturated alkenyl groups based on the total number of moles of alkyl and alkenyl groups present.

21. The structured surfactant system of claim 20, wherein said pharmaceutical or veterinary active ingredient is a hypnotic.

* * * * *